United States Patent [19]
Akiyama et al.

[11] Patent Number: 5,472,437
[45] Date of Patent: Dec. 5, 1995

[54] SANITARY NAPKIN HAVING FLAPS

[75] Inventors: Yoshihiro Akiyama, Tsukui; Shinichi Hatakeyama, Sagamihara, both of Japan

[73] Assignee: Minnesota Mining and Manufacturing Company, St. Paul, Minn.

[21] Appl. No.: 249,060

[22] Filed: May 25, 1994

Related U.S. Application Data

[63] Continuation of Ser. No. 90,468, Jul. 12, 1993, abandoned, which is a continuation of Ser. No. 855,920, Mar. 23, 1992, abandoned.

[30] Foreign Application Priority Data

Apr. 15, 1991 [JP] Japan .................................. 3-082504

[51] Int. Cl.⁶ ............................ A61F 13/15; A61F 13/20
[52] U.S. Cl. ...................... 604/385.1; 604/386; 604/387; 604/389; 604/390
[58] Field of Search .............................. 604/385.1, 386, 604/387, 389, 390, 391

[56] References Cited

U.S. PATENT DOCUMENTS

| | | | |
|---|---|---|---|
| 2,889,038 | 6/1959 | Kalleberg . | |
| 3,643,662 | 2/1972 | McGuire et al. | 604/387 |
| 3,926,191 | 12/1975 | Tritsch . | |
| 3,952,744 | 4/1976 | Aldinger . | |
| 4,168,196 | 9/1979 | Nemeth et al. . | |
| 4,380,450 | 4/1983 | Reich | 604/386 |
| 4,410,325 | 10/1983 | Lare | 604/389 |
| 4,522,870 | 6/1985 | Esmay . | |
| 4,589,876 | 5/1986 | Van Tilburg | 604/385 |
| 4,687,478 | 8/1987 | Van Tilburg | 604/387 |
| 4,701,178 | 10/1987 | Glaug et al. | 604/387 |
| 4,900,320 | 2/1990 | McCoy | 604/387 |
| 4,985,025 | 1/1991 | Lingertat et al. | 604/390 |
| 5,201,727 | 4/1993 | Nakanishi et al. | 604/385.1 X |

FOREIGN PATENT DOCUMENTS

| | | | |
|---|---|---|---|
| 0182692 | 5/1986 | European Pat. Off. . | |
| 0191355 | 8/1986 | European Pat. Off. . | |
| 313426 | 4/1989 | European Pat. Off. | 604/387 |
| 0471587 | 2/1992 | European Pat. Off. . | |
| 60-199446 | 10/1985 | Japan . | |
| 62-129007 | 8/1987 | Japan . | |
| 62-148505 | 9/1987 | Japan . | |
| 1-72218 | 5/1989 | Japan . | |
| 2244910 | 12/1991 | United Kingdom . | |
| WOA8902729 | 4/1989 | WIPO . | |
| 9116873 | 11/1991 | WIPO | 604/387 |

Primary Examiner—Mary Beth O. Jones
Attorney, Agent, or Firm—Gary L. Griswold; Walter N. Kirn; William J. Bond

[57] ABSTRACT

A sanitary napkin having side flaps is disclosed. The sanitary napkin comprises a main napkin body and flaps extending from the right and left sides of said main napkin body, the end of each of said flaps being folded with the back side thereof inside and said folded portions being releasably overlapped with an adhesive portion and a release portion in opposition thereto.

7 Claims, 1 Drawing Sheet

U.S. Patent
Dec. 5, 1995
5,472,437
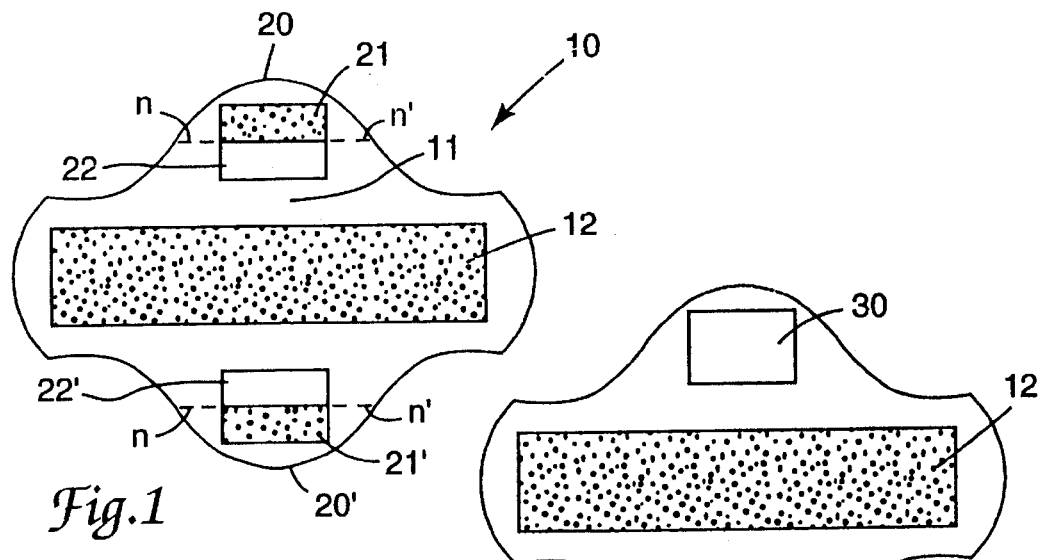
Fig.1
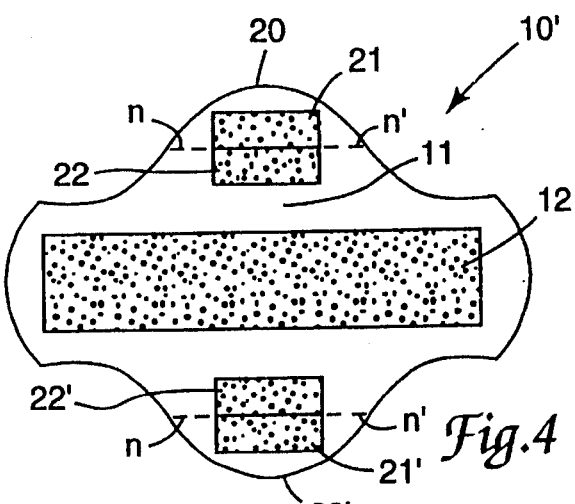
Fig.3
Prior Art
Fig.2
Fig.4
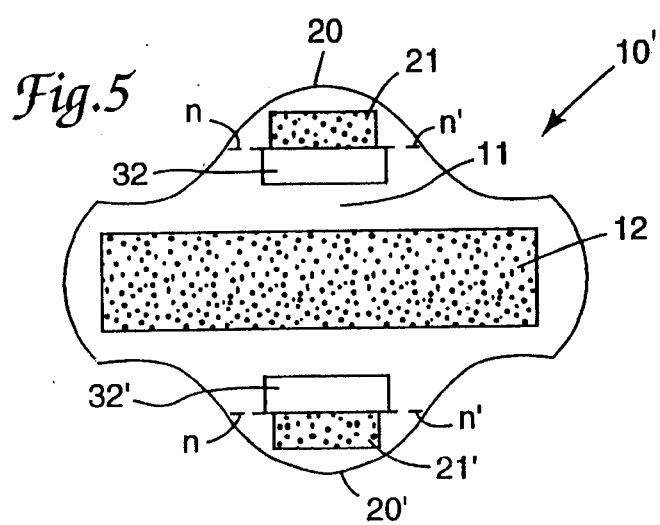
Fig.5

SANITARY NAPKIN HAVING FLAPS

This is a continuation of application Ser. No. 08/090468 filed Jul. 12, 1993, now abandoned, which is a continuation of application Ser. No. 07/855,920, filed Mar. 23, 1992, now abandoned.

FIELD OF THE INVENTION

The present invention relates to a sanitary napkin having flaps extending from the sides thereof.

BACKGROUND OF THE INVENTION

Sanitary napkins having flaps extending from the right and left sides of the main portion thereof to prevent the lateral leakage of menstrual blood and the like, have been developed as disclosed in Japanese Patent Application Kokai (Laid-Open) No. Sho 60-199446. An adhesive is often coated on the back side of the main portion of the sanitary napkin so that the sanitary napkin can be fixed to undergarments. When the sanitary napkin has flaps, the right and left ends of the flaps extend from the undergarment and it is preferable that the flaps are folded backward along the edge of the underwear and the folded portions are fixed to the back side of the underwear edge.

In a sanitary napkin having flaps, adhesive is applied to the back side of the main portion and the flaps thereof and the adhesive is protected by release paper adhered thereto (30, 30' in FIG. 3). In use, the release paper is removed prior to positioning the sanitary napkin for use.

In these known sanitary napkins, the procedures of both removing the release paper and disposing of it are needed in addition to disposing of the packaging material. The flap is flexible in order to function properly. When the sanitary napkin is used after the release papers of the main portion and of the flaps have been removed, accidental contact may arise between the adhesive of the flap and that of the main portion, the adhesives of the flaps, or the adhesive of the flap and portion of undergarment and the sanitary napkin may become unusable.

Therefore, a user generally removes only the release paper of the main portion and disposes of the it, adheres the sanitary napkin to the undergarment and then removes the release papers from the flaps and disposes of them. Even in this case, however, when the release paper is completely removed from the flap, the free end of the flap must be held by a hand different from that used to release the release paper to prevent contact of the adhesive portion with any other portion.

BRIEF DESCRIPTION OF THE INVENTION

The present invention relates to a sanitary napkin having flaps for preventing a lateral leakage of menstrual blood and the like comprising a sanitary napkin having flaps extending from the right and left sides of the main portion of the napkin, the end of each of the flaps being folded with the back side thereof inside and the folded portions being releasably overlapped with an adhesive portion and a release portion in opposition thereto. The release portion may comprise a release agent coated on the back side of the flap, a single coated tape having a release treatment on the back side thereof which is adhered on the back side of the flap, or a second adhesive coated on the back side of the flap, the second adhesive and the adhesive of the adhesive portion being incompatible and non-adhesive with each other.

This provides a sanitary napkin having flaps which can be securely attached to an undergarment without requiring removing and disposing of the release papers of the flaps after the main portion has been adhered to the undergarment. The sanitary napkin of the present invention does not require removal of and disposal of release papers of the flaps and enables the flaps thereof to be easily and securely attached to an undergarment by flatly unfolding and spreading the folded and overlapped portion thereof and adhering adhesive portions to the undergarment. By using a single coated tape, a release portion is easily formed by the tape having a release treatment on the back side thereof. By using the appropriate combination of adhesives, i.e., adhesives which are incompatible and non-adhesive with each other and the adhesive portion and release portion, the release treatment becomes unnecessary.

BRIEF DESCRIPTION OF THE DRAWINGS

FIG. 1 is a plan view of a sanitary napkin of the present invention, wherein the flaps are unfolded and spread flat;

FIG. 2 is a cross sectional view of a sanitary napkin according to the present invention; and FIG. 3 is a plan view of a sanitary napkin having flaps of the prior art.

FIG. 4 is a plan view of a sanitary napkin of the present invention, wherein the flaps are unfolded and spread flat.

FIG. 5 is a plan view of a sanitary napkin of the present invention, wherein the flaps are unfolded and spread flat.

DETAILED DESCRIPTION OF THE INVENTION

The adhesive portions can be formed, for example, from a rubber adhesive or an acrylic adhesive. Further, a double coated tape, double coated tape without a core (transfer tape), a hot melt adhesive, etc., such as are well-known to those skilled in the art, may be used.

The release portions can be formed by coating with a silicone release agent, a urethane release agent, or other release agents as are well-known to those skilled in the art or by selection of a single coated tape having a release coating on the back side thereof.

The folding portion of the flaps, fold line nn' in FIG. 1 is preferably defined longitudinally at substantially the center in the width direction of the flap, but not particularly limited thereto. The configuration of the adhesive portion is preferably similar to that of the portion having the release property, but the latter portion may be a little larger than the former portion, as shown in FIG. 5, so long as the latter portion entirely covers the former portion and they may have different configurations.

It is preferable that the widths of the adhesive portion and the release portion are made to be about one half the width of the flap, respectively and both portions are located as closely as possible so that a pair thereof is positioned on the flap as a whole, but the arrangement thereof are not limited thereto.

A plurality of the adhesive portions and release portions may be disposed on each side of the flap in correspondence to the folding line nn' or the adhesive portions and the release portions may be disposed apart from the folding line nn', respectively The adhesive portion need not always be disposed on the end side of the flap.

Since the sanitary napkin according to the present invention does not require release papers for protecting the adhesive portions of the flaps, removing and disposing of the release papers of the flaps is not needed after the main portion thereof has been adhered to an undergarment and additional attention is not necessary to prevent the adhesive portion of the flap from coming into contact with any other portion, whereby the flap can be securely adhered to an undergarment with one hand.

Examples of the sanitary napkin according to the present invention will be described in more detail with reference to drawings.

EXAMPLE 1

As shown in FIG. 1, a sanitary napkin 10 is provided with flaps 20, 20' extending from the right and left sides of the main portion 11 of the napkin. The end of each flap may be folded along a folding line nn' with the back side thereof inside as shown in FIG. 2. FIG. 1 shows each folded portion being unfolded and spread flat. Adhesive portions 21, 21' and release portions 22, 22' are substantially symmetrically disposed on the folding portions about the center of the folding line nn'.

In FIG. 5 the release portions 32 and 32' are slightly larger than adhesive portions 21 and 21' otherwise the sanitary napkin 10" of FIG. 5 is identical to that of FIG. 1.

An adhesive similar to that used for the adhesive portions 21, 21' on the above flaps can be used as adhesive portion 12 on main portion 11 and adhesive portion 12 is protected by a release paper attached thereto.

FIG. 4 shows a sanitary napkin 10' which similar to sanitary napkin 10 shown in FIG. 1 except release portions 22, 22' are formed from an adhesive which is incompatible and non-adhesive with portions 21, 21'.

EXAMPLE 2

A sanitary napkin 10 was made in the same way as that of Example 1 except that a back side treated single coated tape was used as release portions 22, 22'.

EXAMPLE 3

A sanitary napkin 10 was made in the same way as that of Example 1 except that an acrylic double coated tape having incompatible adhesives which are non-adhesive with each other on the first and second sides was used as the combination of adhesive portions 21, 21' and release portions 22, 22'.

What is claimed is:

1. A sanitary napkin comprising a main napkin body having a body facing face and an opposite backface, the napkin body having flaps extending from the right and left sides of said main napkin body, each of said flaps having a backside said flap backsides facing in the same direction as said napkin body backface, said napkin body backface having a napkin body adhesive portion protected by a release liner, said flaps having a folding line separating a flap release portion and an opposing flap adhesive portion, said flaps being folded along said folding line, such that an end portion of each of said flaps is folded onto an inner portion, such that said release portion releasably contacts said adhesive portion, wherein when a distal end of said flap is pulled said flaps extend into an unfolded state and the adhesive portion on said flap backside is exposed for attachment to an undergarment.

2. The sanitary napkin according to claim 1, wherein said release portion comprises a release agent coated on said backside of said flap.

3. A sanitary napkin according to claim 1, wherein said release portion comprises a single coated tape having a release treatment on the back side thereof which is adhered on the backside of said flap.

4. The sanitary napkin according to claim 1 wherein said adhesive portion is located at said flap end portion.

5. The sanitary napkin according to claim 1 wherein said release portion is located at said flap end portion.

6. The sanitary napkin according to claim 1 wherein said release portion is larger than said adhesive portion.

7. A sanitary napkin comprising a main napkin body and flaps extending from the right and left sides of said main napkin body, the end of each of said flaps being folded to form folded portions with the backsides of each of said flaps forming the inside fold and said folded portions inside folds being releasably overlapped with an adhesive portion and a release portion in opposition thereto, said release portion comprising a second adhesive coated on the backside of said flap, said second adhesive and the adhesive of said adhesive portion being incompatible and non-adhesive with respect to each other.

* * * * *

UNITED STATES PATENT AND TRADEMARK OFFICE
CERTIFICATE OF CORRECTION

PATENT NO. : 5,472,437
DATED : December 5, 1995
INVENTOR(S) : Yoshihiro Akiyama and Shinichi Hatakeyama It is certified that error appears in the above-indentified patent and that said Letters Patent is hereby corrected as shown below:

Col. 2, line 64, "respectively The" should read --respectively. The--.

Signed and Sealed this

Twelfth Day of March, 1996

Attest:

Attesting Officer

BRUCE LEHMAN

Commissioner of Patents and Trademarks